United States Patent
Lim et al.

(10) Patent No.: US 10,940,315 B2
(45) Date of Patent: *Mar. 9, 2021

(54) MULTI-MODAL SYNCHRONIZATION THERAPY

(71) Applicant: Regents of the University of Minnesota, Minneapolis, MN (US)

(72) Inventors: Hubert H. Lim, Minneapolis, MN (US); Craig D. Markovitz, Minneapolis, MN (US); Sarah J. Offutt, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/362,001

(22) Filed: Mar. 22, 2019

(65) Prior Publication Data
US 2019/0282808 A1    Sep. 19, 2019

Related U.S. Application Data

(63) Continuation of application No. 14/395,034, filed as application No. PCT/US2013/026594 on Feb. 18, 2013, now Pat. No. 10,265,527.

(Continued)

(51) Int. Cl.
*A61N 1/36*    (2006.01)
*A61N 2/00*    (2006.01)
(Continued)

(52) U.S. Cl.
CPC ............... *A61N 1/361* (2013.01); *A61F 7/00* (2013.01); *A61F 11/00* (2013.01); *A61H 23/0236* (2013.01); *A61M 21/00* (2013.01); *A61N 1/36025* (2013.01); *A61N 1/36038* (2017.08); *A61N 1/36067* (2013.01); *A61N 1/36071* (2013.01); *A61N 1/36082* (2013.01); *A61N 1/36096* (2013.01); *A61N 1/36167* (2013.01); *A61N 2/002* (2013.01); *A61N 2/006* (2013.01); *A61N 2/02* (2013.01); *A61N 5/0622* (2013.01);
(Continued)

(58) Field of Classification Search
CPC ................ A61N 1/361; A61N 1/36021; A61N 1/36025; A61N 1/36071; A61N 1/36082; A61N 1/36085; A61N 1/36096
See application file for complete search history.

(56) References Cited

U.S. PATENT DOCUMENTS 5,092,835 A    3/1992    Schurig et al.
6,295,472 B1   9/2001    Rubinstein et al.
(Continued)

FOREIGN PATENT DOCUMENTS

WO    2005089470 A2    9/2005
WO    2014145914 A1    9/2014
WO    2017085083 A1    5/2017

OTHER PUBLICATIONS

Berding, G , et al., "Positron Emission Tomography Imaging Reveals Auditory and Frontal Cortical Regions Involved with Speech Perception and Loudness Adaptation", PLOS One 10(6), e0128743, doi:10.1371/journal.pone.0128743, 15 pages (2015).

(Continued)

*Primary Examiner* — Paula J Stice
(74) *Attorney, Agent, or Firm* — Quarles & Brady LLP (57) ABSTRACT

The invention provides methods for treating a neurological disorder or deficit, such as tinnitus and phantom limb pain.

20 Claims, 4 Drawing Sheets

Related U.S. Application Data (60) Provisional application No. 61/625,526, filed on Apr. 17, 2012.

(51) Int. Cl.

| | | |
|---|---|---|
| *A61N 2/02* | (2006.01) | |
| *A61N 5/06* | (2006.01) | |
| *A61H 23/02* | (2006.01) | |
| *A61M 21/00* | (2006.01) | |
| *A61F 7/00* | (2006.01) | |
| *A61F 11/00* | (2006.01) | |
| *A61N 7/00* | (2006.01) | |

(52) U.S. Cl.
CPC .. *A61H 2201/0207* (2013.01); *A61H 2201/10* (2013.01); *A61H 2201/1604* (2013.01); *A61H 2205/027* (2013.01); *A61M 2021/0027* (2013.01); *A61N 1/36036* (2017.08); *A61N 7/00* (2013.01); *A61N 2007/0026* (2013.01); *A61N 2007/0043* (2013.01); *A61N 2007/0073* (2013.01); *A61N 2007/0078* (2013.01)

(56) References Cited

U.S. PATENT DOCUMENTS

| | | |
|---|---|---|
| 7,493,172 B2 | 2/2009 | Whitehurst et al. |
| 7,613,519 B2 | 11/2009 | De Ridder |
| 7,613,520 B2 | 11/2009 | De Ridder |
| 7,756,584 B2 | 7/2010 | Sheffield et al. |
| 7,797,029 B2 | 9/2010 | Gibson et al. |
| 8,433,418 B2 | 4/2013 | De Ridder et al. |
| 9,242,067 B2 | 1/2016 | Shore et al. |
| 9,682,232 B2 | 6/2017 | Shore et al. |
| 10,265,527 B2 | 4/2019 | Lim et al. |
| 10,569,082 B2 | 2/2020 | Shore et al. |
| 10,701,498 B2 | 6/2020 | Lim et al. |
| 2003/0220669 A1 | 11/2003 | Shealy |
| 2006/0036297 A1 | 2/2006 | Seidman et al. |
| 2006/0095088 A1 | 5/2006 | De Ridder |
| 2007/0265683 A1 | 11/2007 | Ehrlich |
| 2008/0021517 A1 | 1/2008 | Dietrich et al. |
| 2009/0287274 A1 | 11/2009 | De Ridder |
| 2010/0004705 A1 | 1/2010 | Kilgard et al. |
| 2010/0256707 A1 | 10/2010 | Ridder |
| 2011/0130615 A1 | 6/2011 | Mishelevich |
| 2011/0172725 A1 | 7/2011 | Wells et al. |
| 2011/0178442 A1 | 7/2011 | Mishelevich |
| 2011/0201977 A1 | 8/2011 | Tass |
| 2012/0203301 A1 | 8/2012 | Cameron et al. |
| 2017/0281900 A1 | 10/2017 | Shore et al. |
| 2017/0318397 A1 | 11/2017 | Lim et al. |
| 2017/0353807 A1 | 12/2017 | Lim et al. |

OTHER PUBLICATIONS

Danilov, et al., "Neurorehabilitation of multiple sclerosis symptoms using cranial nerve non-invasive neuromodulation (CN-NINM): Controlled study", Society for Neuroscience, Abstract, 2 pages (2011).

Engineer, Navzer D., et al., "Reversing pathological neural activity using targeted plasticity", Nature 470, 101-104 (2011) and Research Supplementary Information, 30 pages.

Gloeckner, Cory D., et al., "A New Concept for Noninvasive Tinnitus Treatment Utilizing Multimodal Pathways", 35th Annual International Conference of the IEEE EMBS, Osaka, Japan, Jul. 3-7, 2013.

Koehler, et al., "Stimulus-timing dependence of somatosensory-induced long-term changes in auditory brainstem neural activity", Society for Neuroscience, Abstract, 2 pages (2011).

Lim, Hubert H., "Towards a Neural Prosthesis for Tinnitus: Understanding the Corticofugal Network Involved with Auditory Plasticity", 5th International TRI Tinnitus Conference, Abstract and Presentation, Buffalo, New York, 84 pages (Aug. 19-21, 2011).

Markovitz, "Cortical stimulation for tinnitus suppression may require localized activation of specific regions within the auditory cortex", X International Tinnitus Seminar, Meeting Abstract, Florianpolis, Brazil, Mar. 16-19, 2011.

Markovitz, "Effect of Cortical Stimulation on Neural Firing in the Inferior Colliculus: Towards a Cortical Stimulator for Tinnitus", Tinnitus Research Initiative Conference, Meeting Abstract, Buffalo, NY (Aug. 19-21, 2011).

Markovitz, et al., "Investigating a new neuromodulation treatment for brain disorders using synchronized activation of multimodal pathways", www.nature.com/Scientificreports 5, 9462 DOI: 10.1038/srep09462, 12 pages (2015).

Markovitz, Craig D., et al., "Pairing broadband noise with cortical stimulation induces extensive suppression of ascending sensory activity", J. Neural Eng. 12, 026006, 17 pages (2015).

Offutt, Sarah J., et al., "Is there a neural switch within the midbrain for auditory plasticity?", Society for Neuroscience Meeting, Washington, D.C., Abstract and Poster, 3 pages (Nov. 3, 2011 and Nov. 15, 2011).

Offutt, Sarah J., et al., "Suppression and facilitation of auditory neurons through coordinated acoustic and midbrain stimulation: investigating a deep brain stimulator for tinnitus", J. Neural Engl 11, 1-17 (2014).

Patent Cooperation Treaty, International Searching Authority, Search Report and Written Opinion for PCT/2013/026594, 7 pages, dated May 7, 2013.

Red Badger, "The Engineer (UK), MuteButton receives funding to trial tinnitus treatment device", http://www.freerepublic.com/focus/f-news/2744113/posts, 6 pages (Jul. 2011).

Shore, Susan, et al., "Convergence of Spinal Trigeminal and Cochlear Nucleus Projections in the Inferior Colliculus of the Guinea Pig", Journal of Comparative Neurology 495, 100-112 (2006).

Shore, S. E., et al., "Cross-Modal Interactiions of Auditory and Somatic Inputs in the Brainstem and Midbrain and Their Imbalance in Tinnitus and Deafness", American Journal of Audiology vol. 17, S193-S209 (2008).

Shore, Susan E., et al., "Somatosensory influence on the cochlear nucleus and beyond", Hearing Research 216-217, 90-99 (2006).

Smith, B, et al., "Co-Activation of the Somatosensory and Auditory Pathways to Induce Central Auditory Plasticity as a New Approach for Treating Tinnitus", ARO Abstracts 36, p. 534 (Feb. 16-20, 2013).

Tass, P, "Vibrotactile Coordinated Reset Stimulation for the Treatment of Neurological Diseases: Concepts and Device Specifications", Cureus 9(8), e1535, 16 pages (2017).

Vanneste, Sven, et al., "Transcutaneous electrical nerve stimulation (TENS) of upper cervical nerve (C2) for the treatment of somatic tinnitus", Exp Brain Res 204, 283-287 (2010).

Dehmel, S, et al., "Noise Overexposure AltersLong-TermSomatosensory-Auditory Processing in the Dorsal Cochlear Nucleus—Possible Basis for Tinnitus-Related Hyperactivity?", Journal of Neuroscience 32(5), 1660-171 (2012).

MULTI-MODAL SYNCHRONIZATION THERAPY

CROSS-REFERENCE TO RELATED APPLICATIONS

This application is a continuation of U.S. application Ser. No. 14/395,034, filed Mar. 30, 2015, which is a 35 U.S.C. § 371 application of International Application No. PCT/US2013/026594, filed Feb. 18, 2013, which claims the benefit of priority of U.S. Application Ser. No. 61/625,526, filed Apr. 17, 2012. The entire content of the applications referenced above are hereby incorporated by reference herein.

STATEMENT OF GOVERNMENT SUPPORT

This invention was made with government support under Grant #R03-DC011589 awarded by the National Institutes of Health. The government has certain rights in the invention.

BACKGROUND

About 250 million people worldwide experience chronic tinnitus that can be bothersome on a daily basis. In the U.S. alone, approximately 16 million people have sought medical attention for tinnitus, with 2-3 million experiencing debilitating and even suicidal conditions (e.g., related to annoyance, depression, anxiety, headaches, insomnia). Considering the link between tinnitus and hearing loss, these numbers will continue to rise due to increased noise in our environment, a larger elderly population, and greater noise-based war injuries. In fact, tinnitus is currently the highest service-connected disability for veterans and the top war-related health cost. Unfortunately, there is no cure or reliable treatment for tinnitus. Various drug therapies, neural and mechanical stimulation methods, psychotherapy, and sound treatments have been attempted but with mixed results. Accordingly, methods to treat tinnitus are needed.

SUMMARY OF CERTAIN EMBODIMENTS OF THE INVENTION

As described herein, a non-invasive or minimally invasive electrical stimulation treatment for suppressing tinnitus is provided. The treatment uses a new approach of simultaneously activating multiple auditory and non-auditory neural pathways with transcutaneous or subcutaneous surface stimulation as well as sound stimulation to induce a highly synchronous "shock" in specific auditory, non-auditory and multi-modal brain centers to improve or suppress the subjective percept of the tinnitus.

Accordingly, certain embodiments of the present invention provide a method for treating tinnitus in a patient in need of such treatment, comprising delivering to the patient at least one synchronized stimulation to the brain, wherein the synchronized stimulation comprises stimulation from at least one auditory pathway and stimulation from at least one non-auditory pathway.

Certain embodiments of the present invention provide a method for treating tinnitus in a patient in need of such treatment, comprising delivering to the patient at least one synchronized stimulation to the brain wherein the synchronized stimulation comprises stimulation from at least two non-auditory pathways.

In certain embodiments, the synchronized stimulation involves a stimulus pattern lasting between 0.01 to 100 ms for each activated pathway with a specifically determined time between each activated pathway that ranges between 0-1000 ms.

In certain embodiments, the non-auditory pathway is a sensory pathway from the patient's head, face, ear, eye, nose, mouth, lip, tongue, tooth, neck, body, limb, genital areas, buttocks/anus regions, hand, finger, foot, or toe.

In certain embodiments, the synchronized stimulation comprises stimulation of multiple non-auditory pathways of more than 10 sites across the patient's head, face, ear, eye, nose, mouth, lip, tongue, tooth, neck, body, limb, genital areas, buttocks/anus regions, hand, finger, foot, or toe to achieve targeted brain activation.

In certain embodiments, the synchronized stimulation comprises stimulation of multiple non-auditory pathways of more than 100 sites across the patient's head, face, ear, eye, nose, mouth, lip, tongue, tooth, neck, body, limb, genital areas, buttocks/anus regions, hand, finger, foot, or toe to achieve targeted brain activation.

In certain embodiments, the synchronized stimulation comprises stimulation of multiple non-auditory pathways of more than 1000 sites across the patient's head, face, ear, eye, nose, mouth, lip, tongue, tooth, neck, body, limb, genital areas, buttocks/anus regions, hand, finger, foot, or toe to achieve targeted brain activation.

In certain embodiments, a single synchronized stimulation is delivered.

In certain embodiments, multiple discrete synchronized stimulations are delivered 100 to 10000 ms apart for a total duration ranging from 1 second to 1 hour that can optionally be repeated as many times as needed for treatment.

In certain embodiments, the stimulation from the non-auditory pathway is evoked by non-invasive stimulation.

In certain embodiments, the stimulation from the non-auditory pathway is evoked by transcutaneous electrical stimulation.

In certain embodiments, the stimulation from the non-auditory pathway is evoked by vibration, pressure, heat, optics, magnetic, ultrasound, taste or scent stimulation.

In certain embodiments, the stimulation from the non-auditory pathway is evoked by a single pulse or pulse train.

In certain embodiments, the stimulation from the non-auditory pathway is evoked by a sinusoid.

In certain embodiments, the stimulation from the non-auditory pathway is evoked by a constant or complex shape.

In certain embodiments, the stimulation from the non-auditory pathway is evoked by subcutaneous electrical stimulation.

In certain embodiments, the stimulation from the non-auditory pathway is evoked by epidural, surface, or penetrating cortical stimulation.

In certain embodiments, the stimulation from the non-auditory pathway is evoked by a single pulse or pulse train.

In certain embodiments, the stimulation from the non-auditory pathway is evoked by a sinusoid.

In certain embodiments, the stimulation from the non-auditory pathway is evoked by a contant or complex shape.

In certain embodiments, the synchronized stimulation from the auditory pathway is evoked by sound.

In certain embodiments, the synchronized stimulation from the auditory pathway is evoked by vibration of the head, outer or middle ear structures, cochlea, or head fluids.

In certain embodiments, the synchronized stimulation from the auditory pathway is evoked by one or more pure tone frequencies.

In certain embodiments, the synchronized stimulation from the auditory pathway is evoked by bandwidth filtered sinusoids or noise.

In certain embodiments, the synchronized stimulation from the auditory pathway is evoked by a complex waveform.

In certain embodiments, the synchronized stimulation from the auditory pathway is evoked by electrical stimulation of the auditory nerve.

In certain embodiments, the synchronized stimulation from the auditory pathway is evoked by optical, magnetic, or ultrasound stimulation of the auditory nerve.

In certain embodiments, the synchronized stimulation from the auditory pathway is evoked by electrical stimulation within the brain, including the cochlear nucleus, inferior colliculus, medial geniculate, cortex.

In certain embodiments, the synchronized stimulation from the auditory pathway is evoked by optical, magnetic, or ultrasound stimulation within the brain, including the cochlear nucleus, inferior colliculus, medial geniculate, cortex.

In certain embodiments, the synchronized stimulation from the auditory pathway is evoked by non-invasive electrical, magnetic, or ultrasound cortical stimulation.

In certain embodiments, the synchronized stimulation from the auditory pathway is evoked by epidural, surface, or penetrating cortical stimulation.

In certain embodiments, the stimulation from the auditory pathway is evoked by a single pulse or pulse train.

In certain embodiments, the stimulation from the auditory pathway is evoked by a sinusoid.

In certain embodiments, the stimulation from the auditory pathway is evoked by a constant or complex shape.

BRIEF DESCRIPTION OF THE FIGURES

FIG. 3.

FIG. 6.

DETAILED DESCRIPTION

Certain embodiments of the invention provide a method for treating a patient having a neurological disorder or deficit, comprising delivering to the patient at least one synchronized stimulation to the brain, wherein the synchronized stimulation comprises stimulation from at least one auditory pathway and stimulation from at least one non-auditory pathway.

Certain embodiments of the invention provide a method for treating tinnitus in a patient in need of such treatment, comprising delivering to the patient at least one synchronized stimulation to the brain wherein the synchronized stimulation comprises stimulation from at least two non-auditory pathways.

Certain embodiments of the invention provide a method for treating tinnitus in a patient in need of such treatment, comprising delivering to the patient at least one synchronized stimulation to the brain, wherein the synchronized stimulation comprises stimulation from at least one auditory pathway and stimulation from at least one non-auditory pathway.

Certain embodiments of the invention provide a method for treating a patient having a neurological disorder or deficit (e.g., a phantom precept such as tinnitus or phantom limb pain), comprising delivering to the patient at least one synchronized stimulation to the brain, wherein the synchronized stimulation comprises stimulation from at least one auditory pathway and stimulation that induces anxiety and/or stress in the patient.

Certain embodiments of the invention provide a method for treating a patient having a neurological disorder or deficit (e.g., a phantom precept such as tinnitus or phantom limb pain), comprising delivering to the patient at least one synchronized stimulation to the brain, wherein the synchronized stimulation comprises stimulation from at least one non-auditory pathway and stimulation that induces anxiety and/or stress in the patient.

In certain embodiments, the neurological disorder or deficit is a phanton percept.

In certain embodiments, the phanton percept is tinnitus or a phantom limb percept.

In certain embodiments, the phanton percept is tinnitus.

In certain embodiments, the phanton percept is phantom limb pain.

In certain embodiments, the neurological disorder or deficit is pain, body tremors, motor deficits, hyperacusis, or a psychological or mental disorder.

In certain embodiments, the psychological or mental disorder is obsessive compulsive disorder, depression, stress, a memory or learning disability, a speech impediment, a visual hallucination, or an auditory hallucination.

In certain embodiments, the synchronized stimulation involves a stimulus pattern lasting up to about 1 second for each activated pathway.

In certain embodiments, the synchronized stimulation involves a stimulus pattern lasting between 0.01 to 100 ms for each activated pathway In certain embodiments, a specifically determined time between each activated pathway ranges between 0-1000 ms.

In certain embodiments, in the at least one non-auditory pathway is a sensory pathway from the patient's head, face, ear, eye, nose, mouth, lip, tongue, tooth, neck, body, limb, genital areas, buttocks/anus regions, hand, finger, foot, or toe.

In certain embodiments, the synchronized stimulation comprises stimulation of multiple non-auditory pathways of up to 10 sites across the patient's head, face, ear, eye, nose, mouth, lip, tongue, tooth, neck, body, limb, genital areas, buttocks/anus regions, hand, finger, foot, or toe.

In certain embodiments, the synchronized stimulation comprises stimulation of multiple non-auditory pathways of more than 10 sites across the patient's head, face, ear, eye, nose, mouth, lip, tongue, tooth, neck, body, limb, genital areas, buttocks/anus regions, hand, finger, foot, or toe.

In certain embodiments, the synchronized stimulation comprises stimulation of multiple non-auditory pathways of more than 100 sites (e.g., from 101-200, 201-300, 301-400, 401-500, 501-600, 601-700, 701-800, 801-900, 901-1000) across the patient's head, face, ear, eye, nose, mouth, lip, tongue, tooth, neck, body, limb, genital areas, buttocks/anus regions, hand, finger, foot, or toe.

In certain embodiments, the synchronized stimulation comprises stimulation of multiple non-auditory pathways of more than 1000 sites across the patient's head, face, ear, eye, nose, mouth, lip, tongue, tooth, neck, body, limb, genital areas, buttocks/anus regions, hand, finger, foot, or toe.

In certain embodiments, a single synchronized stimulation is delivered.

In certain embodiments, multiple discrete synchronized stimulations are delivered every 100 to 10000 ms apart (e.g., 100, 200, 300, 400, 500, 750, 1000, 2500, 5000, 7500, or 10000 ms apart) for a total duration ranging from 1 s to 1 hour that can be repeated as many times as needed for treatment.

In certain embodiments, the stimulation from the at least one non-auditory pathway is evoked by non-invasive stimulation.

In certain embodiments, the stimulation from the at least one non-auditory pathway is evoked by transcutaneous electrical stimulation.

In certain embodiments, the stimulation from the at least one non-auditory pathway is evoked by vibration, pressure, heat, optics, magnetic, ultrasound, taste or scent stimulation.

In certain embodiments, the stimulation from the at least one non-auditory pathway is evoked by a single pulse or pulse train.

Visual flashes, images, pressure patterns, complex cognitive or motor tasks, complex or pleasurable smells and tastes, unexpected and transient stimuli, startle stimuli, temperature changing stimuli, complex vibrations may also be used as the stimulation.

In certain embodiments, the stimulation from the at least one non-auditory pathway is evoked by a sinusoid.

In certain embodiments, the stimulation from the at least one non-auditory pathway is evoked by a constant or complex shape.

In certain embodiments, the stimulation from the at least one non-auditory pathway is evoked by subcutaneous electrical stimulation.

In certain embodiments, the stimulation from the at least one non-auditory pathway is evoked by epidural, surface, or penetrating cortical stimulation.

In certain embodiments, the stimulation from the at least one non-auditory pathway is evoked by a single pulse or pulse train.

In certain embodiments, the stimulation from the at least one non-auditory pathway is evoked by a sinusoid.

In certain embodiments, the stimulation from the at least one non-auditory pathway is evoked by a contant or complex shape.

In certain embodiments, the synchronized stimulation from the at least one auditory pathway is evoked by sound.

In certain embodiments, the synchronized stimulation from the at least one auditory pathway is evoked by vibration of the head, outer or middle ear structures, cochlea, or head fluids.

In certain embodiments, the synchronized stimulation from the at least one auditory pathway is evoked by one or more pure tone frequencies.

In certain embodiments, the synchronized stimulation from the at least one auditory pathway is evoked by bandwidth filtered sinusoids or noise.

In certain embodiments, the synchronized stimulation from the at least one auditory pathway is evoked by a complex waveform.

In certain embodiments, the synchronized stimulation from the at least one auditory pathway is evoked by electrical stimulation of the auditory nerve.

In certain embodiments, the synchronized stimulation from the at least one auditory pathway is evoked by optical, magnetic, or ultrasound stimulation of the auditory nerve.

In certain embodiments, the synchronized stimulation from the at least one auditory pathway is evoked by electrical stimulation within the brain, including the cochlear nucleus, inferior colliculus, medial geniculate, cortex.

In certain embodiments, the synchronized stimulation from the at least one auditory pathway is evoked by optical, magnetic, or ultrasound stimulation within the brain, including the cochlear nucleus, inferior colliculus, medial geniculate, cortex.

In certain embodiments, the synchronized stimulation from the at least one auditory pathway is evoked by non-invasive electrical, magnetic, or ultrasound cortical stimulation.

In certain embodiments, the synchronized stimulation from the at least one auditory pathway is evoked by epidural, surface, or penetrating cortical stimulation.

In certain embodiments, the stimulation from the at least one auditory pathway is evoked by a single pulse or pulse train.

In certain embodiments, the stimulation from the at least one auditory pathway is evoked by a sinusoid.

In certain embodiments, the stimulation from the at least one auditory pathway is evoked by a constant or complex shape.

In certain embodiments, the method may further comprise delivering a stimulus that induces anxiety and/or stress in the patient.

In certain embodiments, the stimulus that induces anxiety and/or stress is a specifically-delivered unexpected stimulus, such as an uncomfortable stimulus.

In certain embodiments, the stimulus that induces anxiety and/or stress is a specifically-delivered stimulus that induces a startle response.

As described herein, a midbrain region (inferior colliculus) as well as a brainstem region (reticular activating nuclei) has been discovered that can be stimulated, e.g., directly stimulated with electrical current, combined with acoustic stimulation to shift the firing patterns of neurons within the central auditory system. This stimulation is able to shut off or alter neural changes resembling the types of activity observed in tinnitus animals. As described herein, it may be possible to 'turn off' the abnormal neural changes observed in tinnitus, thus providing a method for suppressing tinnitus in a large patient population. Although it is possible to directly stimulate these midbrain or brainstem regions with surface and penetrating arrays implanted into the head in severe tinnitus patients, a non-invasive method to achieve this effect may also be used to treat a larger patient population. These midbrain and brainstem regions are multi-modal brain centers that receive projections from various regions all over the head and body (e.g., skin surface and muscles coming from the face, eyes, head, pinna, neck, mouth, tongue, lips, upper extremities, upper spinal cord, genital areas, and other regions not yet identified) as well as projections from the cortex. The genital areas have significant projections to pleasure, limbic, and arousal brain centers that can be activated non-invasively and combined with acoustic stimulation to shift activity in the auditory pathways to suppress tinnitus. In certain embodiments, the patient (e.g., a human male or human female) receiving the stimulation to the genital area is sexually aroused, and in certain embodiments the patient is not sexually aroused. The midbrain region is involved in multi-modal processing (e.g., audio-visual orienting reflex). The brainstem region is involved in arousal and sleep-wake cycles. It has been discovered that it is possible to non-invasively (e.g., transcutaneously) stimulate these different regions and projection pathways using surface electrodes on the skin. Other options for stimulation include using heat, ultrasound, optics, magnetic, mechanical, etc., instead of electrical current. A newly discovered embodiment is to transiently stimulate these different regions simultaneously, or with some interval, so that the inputs reach these different brainstem and/or midbrain centers at the same time to cause a synchronized "shock" pattern that can then modify neurons, e.g., tinnitus-affected neurons. Activation of these different pathways can also activate other brain targets involved with plasticity and reinforcement that can modify neurons, e.g., tinnitus-affected neurons.

Stimulation of the genital area will be able to access the arousal/limbic inputs that can reinforce the neural changes. The tongue, face, foot sole, finger pads, and spinal back area have more sensitivity and smaller receptive fields, so those areas may provide greater ability for coordinated and thus targeted brain activation. The shoulder, neck, and ear are involved with the orienting reflex response and are more tightly coupled with the auditory system and could be effective in modulating auditory activity.

In certain embodiments, at least one of the following brain areas is the 'target' brain area for delivering the synchronized stimulation. Certain auditory brain areas include the cochlear nucleus, the lateral lemniscus, the inferior colliculus, the medial geniculate nucleus and the auditory cortex. Certain non-auditory brain areas include the-reticular activating nuclei (e.g., the pontomesencephalic tegmentum), the limbic nuclei (e.g., the amygdala, hippocampus, cingulate gyms, nucleus accumbens), the basal forebrain, the cholinergic system and the noradrenergic system. Certain of these areas are described in FIG. 1.

The number of areas stimulated can, in certain embodiments, be up to 10, from 10-100 or from 100-1000, and in certain embodiments, more than 1000. This will effectively stimulate numerous sites across different surface regions in a temporally coordinated pattern. This provides coordinated timing of transient stimuli between multiple sites that are effectively synchronized with acoustic stimulation to provide the synchronized stimulation. Direct nerve or brain stimulation may be used in certain embodiments because, e.g., there are patients implanted in these regions for hearing restoration who also have tinnitus. It would be possible to directly stimulate these patient's brains, combined with stimulation of the other auditory and non-auditory sensory pathways.

While not intended to be a limitation of the present invention, it is believed that the brain maintains memory of how things used to be even though the brain may adapt and change to code for new features. In other words, there are fixed "original" representations in the brain that are continuously maintained to keep some order in the brain and new representations (whether normal plasticity to learning or abnormal due to disease states, such as tinnitus) that co-exist simultaneously. The brain can then switch between these states quite easily and rapidly. In this context, the auditory system is described herein for the first time as a fixed/plastic organization with at least one neural switch. As such, the concept and method to non-invasively activate this neural switch to return the abnormal brain back to a normal state to suppress tinnitus is described herein.

Certain embodiments provide a non-invasive method to suppress tinnitus by using surface stimulation. If necessary, electrodes can be implanted directly onto or into nerves with minimally invasive techniques. For more severe cases, brain surgery can also be considered to implant surface and/or penetrating electrode arrays to directly stimulate the different midbrain and brainstem regions involed with this neural switch. The fact that other brain regions (e.g., thalamus, cortex, limbic nuclei, basal forebrain) are interconnected with these brainstem and midbrain regions and contribute to the tinnitus effect, other multi-modal projection pathways can be stimulated non-invasively or invasively.

There have been attempts at presenting acoustic stimulation to either restore some of the hearing loss driving the tinnitus or to directly mask the tinnitus. However, simply using acoustic stimulation does not appear to be powerful enough to fully restore lost frequency representations. As described herein, an important difference between previously-proposed treatments and what is proposed herein is that it is not necessarily an object of the invention to neuromodulate and retrain the brain back to normal. What is proposed herein is a new concept that the brain has its original state hidden under an abnormal diseased representation. The methods provided herein "shock" the brain to switch back to its original state. This is not trying to retrain the brain, but induce a "shock" to reset it back. Although it is tempting to relate this to defibrillation, there are some distinct differences. Fibrillation is where the heart goes from being normal to abnormal firing, and then the heart is shocked to depolarize all the neurons at once with a slight pause to then go back to its normal state. For tinnitus, there are situations where there can be a sudden shift of the neurons from a normal to abnormal state but usually it involves some changes that occur over time that then reorganize the brain to represent this abnormal state. So there is a new representation of sound coding in which both the old and new co-exist at the same time, but the old state is hidden. The idea is then to switch the brain back to the normal state. While not necessarily an object of the invention, it is proposed that the normal brain actually does this in learning new sound coding strategies but also happens for abnormal diseased states. Treatment can be achieved, e.g., with a single or several highly synchronous stimuli (e.g., shocks) combined with acoustic stimulation. This paradigm can be repeated periodically over hours or days or weeks, as needed. In one aspect, electrodes may be permanently implanted under the skin (e.g., wireless micro-electrodes) for repeated presentation as needed by the patient.

Even if, for the sake of argument, others may have proposed combining acoustic stimulation with vagal nerve or tongue stimulation, and other groups for the sake of argument may have proposed stimulating non-auditory regions, none has yet proposed to stimulate these regions to induce a highly synchronized "shock" in the brain. As such, the acoustic stimulation is combined with the electrical stimulation so that the projection pathways to the neural switch regions are synchronously activated, whether using electrical, acoustic, or any other form of activation. For example, the cochlea or auditory nerve could be stimulated for those with significant hearing loss or even stimulate the nerve non-invasively or with minimal invasiveness even in patients with hearing. In certain embodiments, the auditory and non-auditory cortex are stimulated (invasively or non-invasively) in combination with another pathway to induce a synchronous shock.

Synchronized stimulation refers to transient stimulation (e.g., 0.01-100 ms) of at least two different pathways in a specific time relative to each other (e.g., 0-1000 ms). The timing is designed and optimized to induce effective activation of one or more specific brain regions to affect the tinnitus percept while other brain regions are not effectively activated because the timing is not optimized for those regions. In turn, this allows for targeted brain activation without having to actually implant and stimulate invasively within those regions. Effectively refers to the ability to alter the tinnitus percept to a subjectively improved state (e.g., not only suppression but also any alteration that could still improve the subjective tinnitus state).

In certain embodiments, the auditory and non-auditory cortex will be stimulated (invasively or non-invasively) in combination with synchronized stimulation of the other pathways described herein to induce a "shock" within the brain. Cortical stimulation is one possible pathway.

In some embodiments, the synchronized stimulation does not comprise vagal stimulation.

In some embodiments, the synchronized stimulation does not comprise stimulation of the tongue.

Previous Tinnitus Treatments

Unfortunately, there is no cure or reliable treatment for tinnitus. Various drug therapies, electrical and mechanical stimulation methods, psychotherapy techniques, and sound treatments have been attempted but with mixed results. Several types of drugs and substances (e.g., anti-anxiety: Xanax; anti-depressants: nortriptyline; vitamins: zinc; herbs: Gingko biloba) have alleviated the tinnitus percept in some individuals, but this benefit is likely due to a reduction in the psychological feelings towards the tinnitus or a placebo effect. It has not been clear which neural mechanisms should be targeted to suppress tinnitus. Similarly, psychotherapy treatments have focused on improving the patient's ability to cope with the tinnitus and have resulted in variable outcomes. Acoustic therapy has attempted to mask the actual phantom sound percept. However, this requires continuous presentation of another sound source and upon termination, the tinnitus percept returns.

Figure 1:
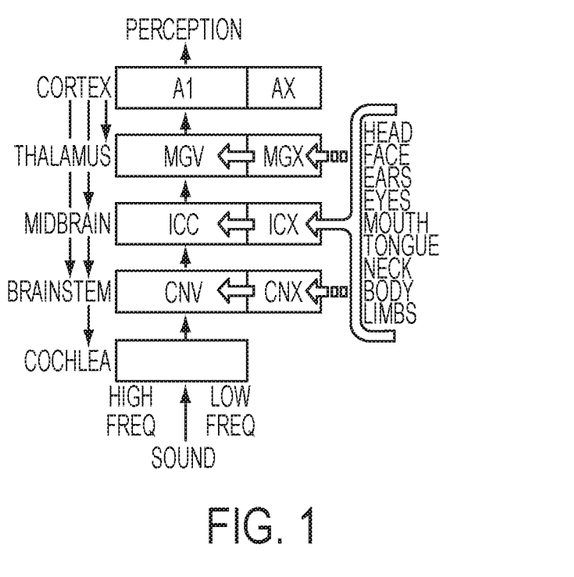
FIG. 1. Simplified schematic of ascending and descending auditory system. CNV, ICC, MGV and A1 are the main ascending auditory nuclei and spatially organized based on sensitivity to different frequencies, while CNX, ICX, MGX and AX correspond to the outer regions involved with multi-modal processing. The listed non-auditory pathways project to ICX and other relevant regions, including cortical, limbic and arousal centers (e.g., pontomesencephalic tegmentum, amygdala, basal forebrain, somatosensory cortex), that can be non-invasively stimulated to modulate ascending activity along the central auditory pathways and suppress tinnitus.

More recently and based on an increased understanding of the causes of tinnitus (described herein) and its link to abnormal changes within the central auditory system, creative acoustic and electrical stimulation methods are being investigated to reverse these abnormal patterns back to normal. Tinnitus is currently viewed as a brain phenomenon in which different types of causes all lead to some reorganization of the central auditory system to elicit the phantom percept. The most common type of tinnitus is associated with noise-induced hearing loss. The auditory system consists of neurons that are spatially ordered based on their sensitivity to different frequencies (i.e., tonotopic organization) within each nucleus from the cochlea up to the auditory cortex (FIG. 1). High levels of noise will damage neurons in the cochlea coding for specific frequency components, eliminating excitatory and inhibitory inputs into more central regions representing those frequencies. Neurons coding for those lost frequencies also become more sensitive to other frequencies. The overall imbalance of inputs initiates a cascade of neural changes throughout the auditory system, such as tonotopic reorganization (e.g., expanded frequency regions), increased firing, over-synchrony across neurons, and abnormal bursting patterns. These changes can be most prevalent in neurons coding for the lost frequencies, which can match the range of frequencies associated with the tinnitus percept. The second most common type of tinnitus is associated with head and neck injuries in which damage to non-auditory neural pathways, which project to auditory neurons, causes an imbalance in the excitatory and inhibitory networks within the central auditory system and leads to a phantom percept. Tinnitus can also develop through dysfunction of non-auditory networks associated with limbic and cognitive centers that feed back into and alter the auditory system.

Considering the neural changes associated with tinnitus, several methods have attempted to restore the lost input driving those changes or neuromodulate the tinnitus-affected neurons to induce sufficient plasticity that would suppress the phantom percept. For those with sufficient hearing, headphones or hearing aids attempt to amplify and fill in missing acoustic information to drive the brain back to normal through plasticity. Rather than fill in the missing acoustic information, other techniques have attempted to modulate and fix the tinnitus-affected neurons through neural stimulation, such as cortical activation using transcranial magnetic stimulation or epidural surface stimulation. Cortical stimulation modulates neurons within the auditory cortex and activates the massive descending network to subcortical neurons that are all contributing to the tinnitus percept. There are also many non-auditory pathways (e.g., from the head, face, body, limbs) that project onto cortical and subcortical auditory neurons. Some of these pathways have been activated with transcutaneous electrical stimulation or acupuncture to modulate neurons in multi-modal centers that can then alter tinnitus-affected neurons. However, these treatments have been unreliable.

Rationale

All of the plasticity-based methods described above have provided mixed results in which some patients may seem to experience a reduction of their tinnitus while others experience no changes or even an increase in their tinnitus. One major hurdle to these methods is that there are numerous types of tinnitus that have a wide range of causes and time courses. Each tinnitus brain may have experienced a different sequence of neural changes and have different capabilities for enabling sufficient plasticity to the different treatments. Furthermore, these different methods are only able to crudely or indirectly activate the necessary auditory pathways to restore back the normal state, which itself consists of an intricate organization. For example, it is unclear how stimulation of the tongue would indirectly transmit features to the auditory brain that are sufficient to restore the intricate sound features that have been lost through the natural hearing pathway. It would seem that stimulation of the tongue could modify some auditory neurons through plasticity but not in such a precise way to restore back the detailed original organization. In terms of neuromodulation, it is unclear how crude surface cortical stimulation would be able to activate clusters of cortical neurons and descending pathways in a precise manner to sufficiently drive different central auditory neurons located in specific regions back to normal.

Rather than presume that these various stimulation treatments were able to somehow drive precise plasticity to restore normal auditory function, the current fundamental understanding of how the brain maintains and adapts its sensory representation to relevant or persistent stimuli under normal and pathological conditions was questioned, as described herein. It was questioned whether the brain maintains a continuous representation of its original state, at least for fundamental features, that is simply suppressed during the development of new learned or pathological states. In this way, the original representation could be recalled if the appropriate neurons were activated, mimicking a "neural switch" rather than a typical plasticity mechanism as proposed for these previous treatments. During tinnitus, the driving source may be preventing the neurons from returning to their original state, but with appropriate activation of certain neural pathways, the brain may then be able to switch back to normal.

No studies have investigated or demonstrated dual fixed-plastic representations for tonotopy or other neural firing properties, such as spontaneous rates and synchrony, within the central auditory system. It was predicted that tonotopy would exhibit this dual state behavior considering that every nuclei along the main ascending auditory system has a frequency organization (i.e., the most fundamental feature of the auditory system; FIG. 1).

As described herein, there are pieces of evidence that collectively form a reasonable argument for the existence of fixed-plastic states for different features within the auditory brain. More importantly, if a neural switch for tinnitus-related states (e.g., for tonotopy and spontaneous firing and synchrony across neurons) can be identified and activated through non-invasive stimulation methods to reset altered neurons back to normal, this would have a significant clinical impact for the large number of tinnitus patients. With these thoughts and justifications in mind, a search for this neural switch was undertaken. Since then, the important role of the descending projections from the primary auditory cortex (A1) to IC in enabling physiological and behavioral plasticity for sound localization and frequency tuning has been investigated. Through the massive ascending and descending interconnections between all the auditory nuclei (FIG. 1), neural changes within IC would then be reflected throughout the central auditory system, including the auditory cortex. Unfortunately, there were no studies describing the detailed anatomical or functional spatial organization of projections from A1 to IC to understand how plasticity could be enabled through this pathway. Thus, experiments were conducted to anatomically and functionally map these projections by electrically stimulating throughout A1 and recording the effects in different locations across IC using multi-site electrode arrays. It has been demonstrated that A1 projects to the central region of IC (ICC) in a precise tonotopic pattern (e.g., a 10 kHz sensitive A1 neuron mainly projects to and excites a 10 kHz ICC neuron). There appears to be distinct locations within A1 that project to distinct locations within ICC representing parallel descending pathways. It was also observed that A1 has a large and diffuse projection pattern throughout the outer IC (ICX), which further projects to ICC (FIG. 1). Based on these findings, it was hypothesized that the direct A1-to-ICC projections sculpt the fine plastic changes within ICC that is reinforced by broad input from the A1-to-ICX pathway. In other words, ICX serves some gating function to enable plasticity within ICC but can also prevent or reset any new changes. Thus, it appeared to be a potential region for the neural switch.

Figure 2:
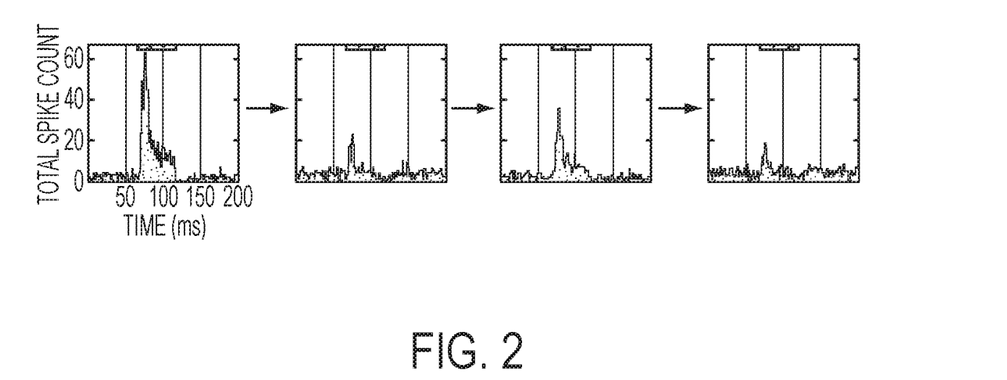
FIG. 2. Post-stimulus time histograms of multi-unit spike activity recorded on the same ICC site in response to an 8 kHz pure tone (bar; 30 dB SPL). Spontaneous and acoustic-driven spiking activity is shown. First arrow shows how the activity changes after repeated ICX electrical stimulation (100 µA, 205 µs pulse) synchronized with 8 kHz pure tone stimulation (30 dB SPL). Second arrow shows recovery of response back towards the initial response simply by waiting (e.g., minutes to hours), supporting that the brain maintains some fixed reference representation that automatically drives the system back to a normal state.

Therefore, the next step was to directly stimulate ICX and attempt to identify a neural switch mechanism by measuring the activation effects within ICC. After much research, a way to switch neural states within ICC was discovered by electrically stimulating the ICX combined with acoustic stimulation in a precisely timed manner. FIG. 2 shows how spiking activity within the ICC can be altered or suppressed after the synchronized ICX-acoustic stimulation. The ICX was stimulated with an electrical pulse and the acoustic stimulus was a pure tone. The timing was synchronized such that the activity induced by each modality arrived at the ICC site at a similar time, thus achieving synchronized activation. After repeated activation with the synchronized paradigm, the ICC activity was altered (first arrow). However, without providing any additional input, the system began to return back to its original response (second arrow) supporting that the brain maintains a reference state that drives the system back to normal. The brain could be repeatedly altered with the synchronized stimulation (last arrow) and then allowed to recover after a waiting period. It is possible that appropriate brain activation could speed up the recovery period.

Figure 3:
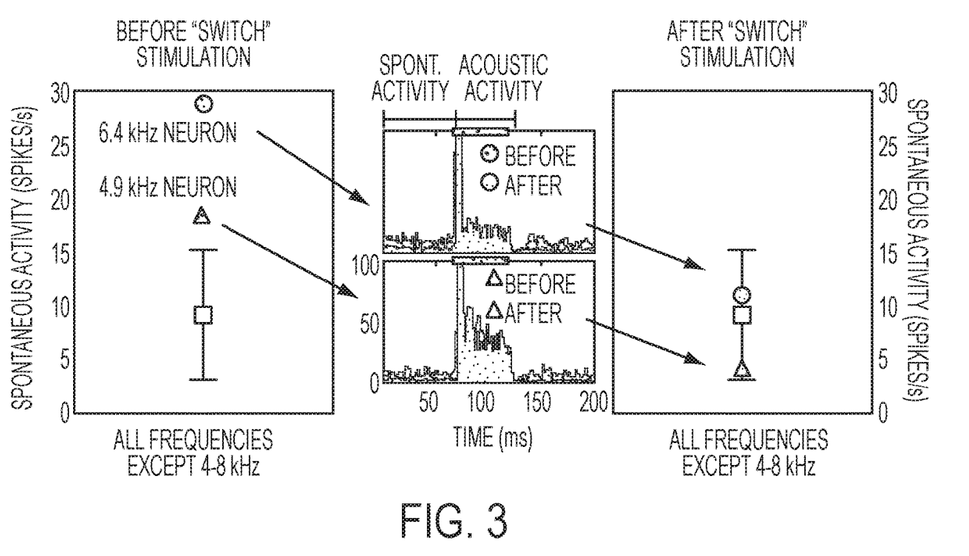
FIG. 3 depicts an example from one noise-damaged animal in which using the synchronized stimulation paradigm reduced the elevated spontaneous spiking activity back to a normal range without altering the acoustic-driven activity. Several neurons sensitive to 4-8 kHz show elevated spontaneous activity compared to those outside that frequency range (mean and S.D., n=39) consistent with previous studies. "Neuron" refers to multi-unit activity recorded on a site.

In FIG. 2, the brain was altered to artificial synchronized stimulation (e.g., for 10 minutes) and then began recovering back to its normal state. In a pathological brain state, the normal state is somehow unable to drive the neurons to its original state. The question arose as to whether the synchronized stimulation paradigm could alter and reverse brain activity that experienced long-term changes associated with a pathological state. It has been shown that presenting a loud (>124 dB SPL) pure tone for over one hour can induce a severe hearing loss at and slightly above that pure tone frequency. These animals then develop hyperactivity across many neurons sensitive to those compromised frequencies within multiple auditory nuclei, including the ICC, which leads to a tinnitus that matches those frequencies. To investigate this further, hearing loss was induced in three animals with a 4 kHz pure tone presented at ~120 dB SPL for one hour and they developed the highest ICC thresholds between approximately 4 to 8 kHz. Elevated spontaneous firing rates were observed in several ICC neurons tuned to those frequencies. Encouragingly, the elevated spontaneous activity was suppressed into a normal range using the synchronized paradigm described herein (FIG. 3). What was even more surprising was that it was possible to suppress the spontaneous activity, presumably linked to tinnitus, without affecting the acoustic-driven pattern. This is important to ensure suppression of tinnitus without altering normal auditory coding function. Overall, these initial results demonstrate that the synchronized stimulation paradigm can suppress elevated firing patterns, similar to those observed in tinnitus animals, back to a normal range.

Additional research focuses on performing neurophysiology and perceptual experiments in guinea pigs to refine the therapy and confirm its effectiveness and safety in suppressing tinnitus. In the early stages of the project, plasticity experiments will be performed to demonstrate that a fixed-plastic state exists for tinnitus-related features and that the brain can switch states through this ICX neural switch. Additional switching mechanisms within the brainstem and thalamus (FIG. 1) will also be examined. Both of these regions exhibit neural changes to tinnitus and receive descending projections from auditory cortex that are involved with plasticity. Thus, stimulation of the outer portions of these regions (e.g., CNX and MGX) involved with descending plasticity could also serve to switch activity within their main ascending pathways (e.g., CNV and MGV). There are also non-auditory regions that project to the auditory system, including the reticular activating system, the limbic nuclei, and basal forebrain, that can also be stimulated to switch states with the auditory system linked to tinnitus. The ability to stimulate the reticular activating system (i.e., pontomesencephalic tegmentum, PPT) to be able to shift coding properties within the ICC has been demonstrated. Once this neural switch mechanism is confirmed across these multiple brain regions, then their ability to switch states in hearing loss and different tinnitus animals will be determined. Tinnitus can be induced by exposing animals to very loud sounds for a certain period of time that damages their peripheral system and causes central plastic reorganization leading to the phantom percept. Tinnitus can also be induced with ototoxic drugs (e.g., salicylate, such as aspirin) administered to the animal. Both of these methods yield several conditions resembling those experienced in humans who have developed tinnitus. The goal will be to demonstrate that stimulation of different neural switch regions, either individually or collectively, reverses the neural changes caused by tinnitus to suppress the phantom percept regardless of its cause or time course. Neural changes can be assessed using multi-site extracellular recordings across multiple brain regions (e.g., >100 simultaneous sites) and perceptual effects using the startle response test, which is a sound reflex paradigm described later.

An important component of this project is ultimately to activate the neural switch regions non-invasively. One embodiment includes non-invasively activating ICX, CNX, MGX, reticular activating nuclei, limbic nuclei, and/or other neural switch centers using multi-modal transcutaneous stimulation. Direct electrical stimulation of the brain induces a highly synchronous shock that simultaneously activates cell bodies and passing fibers within a specific region, which is what was induced during ICX stimulation to achieve the effects in FIGS. 2 and 3. Fortunately, ICX is involved with multi-modal processing (e.g., audio-visual orienting reflex) and receives converging inputs from all over the head, face, ears, eyes, mouth, tongue, neck, body, and limbs (FIG. 1).

The trigeminal nerve, dorsal root of spinal nerve, optic nerve, auditory cortex, and somatosensory cortex all project to ICX. Similarly, many of these pathways have shown to project to the CNX, MGX, reticular activating system, and other potential neural switch centers (FIG. 1). In certain embodiments, multiple surface electrodes are positioned over the head, face, ears, eye regions, mouth, tongue, neck, body, genital areas, limbs, foot sole, and digits (e.g., up to 10, 20, 100 or 1000). These electrodes can then be stimulated simultaneously or with specifically-timed delays to activate as many of the non-auditory pathways and induce a highly synchronous shock in those neural switch regions. Non-invasive cortical stimulation (e.g., surface or transcranial magnetic stimulation) to activate the descending auditory and somatosensory cortex projections or shining light into the eye to activate the optic nerve projections, in addition to transcutaneous stimulation of the other regions, are possible. Other forms of stimulation may be cognitive tasks, motor task/movement, flashes, images, complex pressure patterns, temperature changes, scents, tastes, etc. To further drive the neural switch, this electrical shock is combined with an acoustic stimulus, e.g., that can be presented via headphones. In the animals, subcutaneous needles and even direct nerve stimulation can be used to identify optimal locations as well as appropriate timing across sites. After assessing the safety of the treatment over longer periods of time (i.e., safe current levels to avoid tissue damage and seizures, neural adaptation and reliability over time, specificity to cause only auditory state changes), these findings can be extrapolated to human patients.

Figure 4:
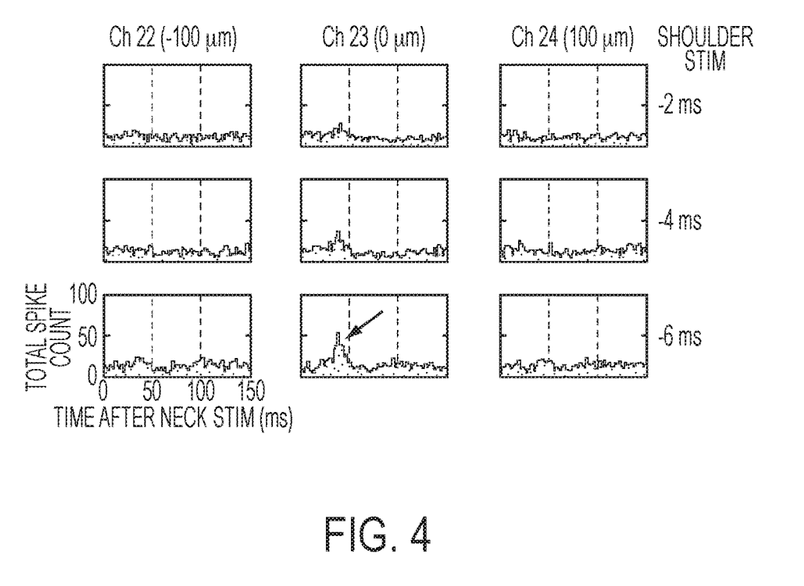
FIG. 4. Data showing spiking activity recorded in ICX for an electrical pulse (205 µs phase) of the neck (450 µA). The shoulder was stimulated 2, 4, or 6 ms before the neck (rows; 400 µA) and the activity across 3 sites 100 µm apart is shown (columns). Arrow points to largest stimulus-evoked response for the −6 ms delay that becomes weaker for the other delays. Stimulation across body sites elicits activity in ICX that depends on recording location and inter-site delay.
Figure 5:
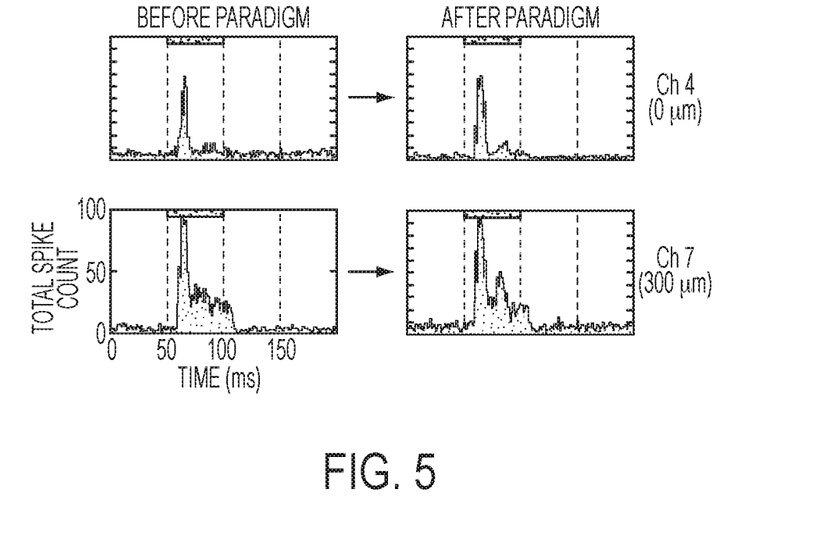
FIG. 5. Data of spiking activity recorded on 2 different sites in ICC (300 µm apart) in response to acoustic stimulation (5 kHz tone, 60 dB SPL, bar=duration) before and after our synchronized body-sound stimulation paradigm for several minutes (repeated 2/s). Ch7 shows significant changes in the temporal pattern of activity. Ch4 shows slight changes in the response onset but significant suppression of spontaneous activity, suggesting elevated activity caused by tinnitus could be suppressed using this method.
Figure 6:
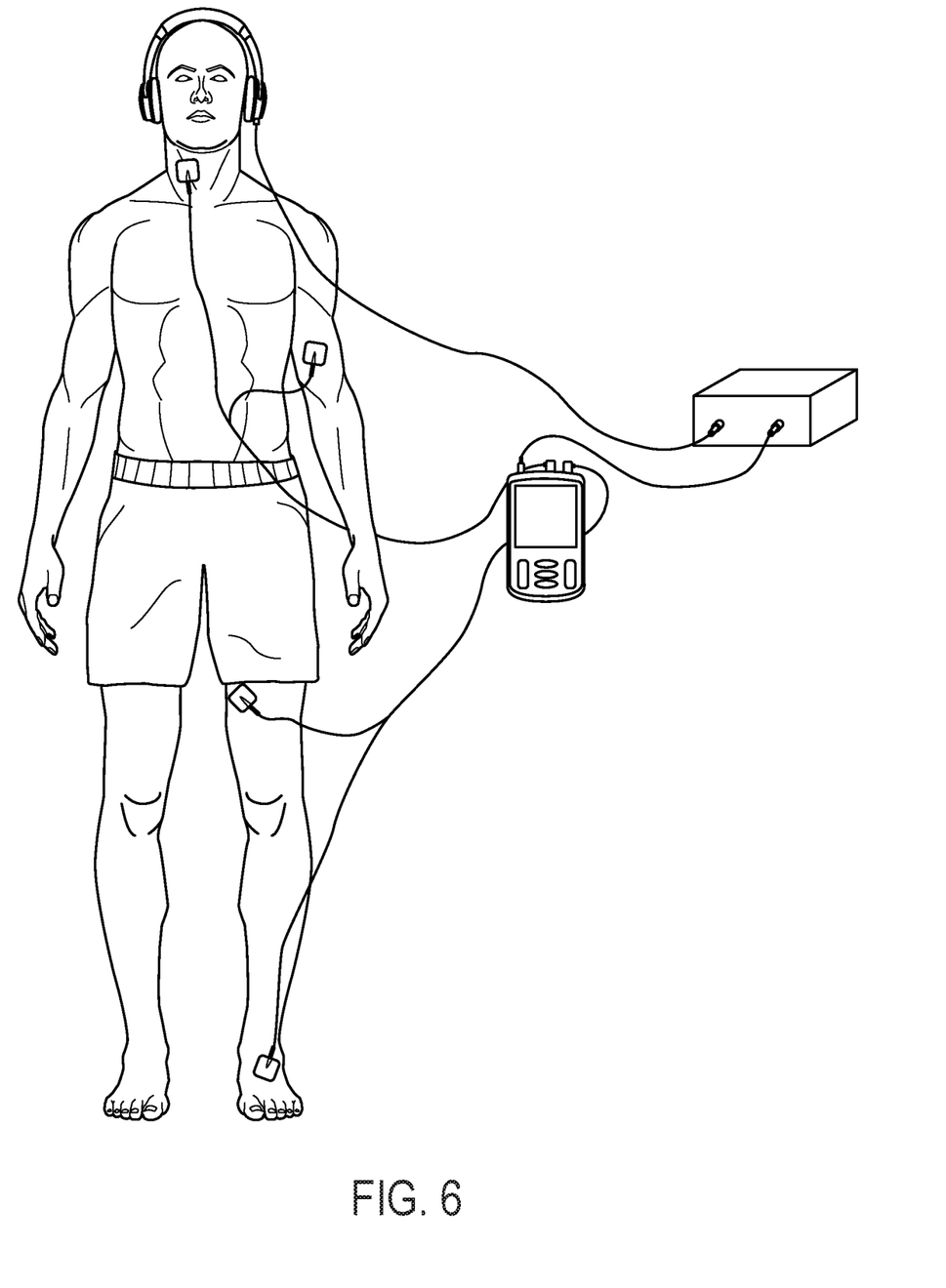
FIG. 6 depicts aspects of the methods described herein for treating a patient having tinnitus with synchronized stimulation, which synchronized stimulation includes auditory stimulation delivered using headphones and non-auditory stimulation caused by transcutaneous electrical nerve stimulation (TENS), which synchronized stimulation is delivered by a device having a user interface.

In animals, the ability to actually activate and alter coding properties in the auditory system through surface body synchronized stimulation is described. FIG. 4 shows an example of stimulating a local region of the neck and left shoulder with electrical biphasic pulses through needle electrodes that were precisely timed 6 ms apart to elicit synchronized activity in ICX that was weaker or absent with a different delay (e.g., 2 or 4 ms). Stimulation of each site individually caused activation across different ICX regions. It was also possible to alter spontaneous and sound-driven spiking activity within ICC after the synchronized activation paradigm (FIG. 5). These results provide consistent evidence for the ability to alter coding properties within the auditory system in response to coordinated stimulation across the body and ear input, and its potential ability to suppress tinnitus.

Multi-Modal Non-Invasive Neural Shock Therapy

In the past decade, the brain stimulation field has grown rapidly with more than 75,000 patients implanted with a penetrating or surface array within various brain regions for treating numerous neurological conditions (e.g., tremors, pain, tinnitus). However, these brain stimulation approaches can only be used in a limited patient population due to their invasiveness, need for advanced surgical resources, time-consuming fitting by trained personnel, and high cost. Furthermore, it is not possible to re-insert the array into numerous locations to identify optimal regions for stimulation to deal with patient variability. There have been a few noninvasive attempts at stimulating the brain to address some of the issues above, including transcranial magnetic stimulation (TMS) and transcranial direct current stimulation (tDCS). For TMS, a magnetic coil is positioned over the head to induce current within the brain. tDCS applies a constant current through the skull through surface electrodes to alter the depolarization state of neurons. Both TMS and tDCS activate a large volume of mostly cortical neurons that is unavoidable when noninvasively activating through the skull. The comparison between TMS or tDCS versus direct brain stimulation highlights the critical trade-off between noninvasiveness versus specificity that has not yet been resolved.

An innovation described herein is a low-cost treatment that achieves both noninvasiveness and specificity. It takes advantage of the dense and coordinated interconnectivity across sensory, motor, cognitive, and limbic centers. One center may exhibit abnormal activity driving the neurological disorder. The goal of the treatment is to activate specific pathways related to the other modalities and with appropriate timing to then modulate and 'fix' the abnormal region. This assumes that these different pathways can interact and induce plasticity across centers, which is expected considering the necessity for precise coordination and reinforcement among these modalities during daily function and survival. Each neuron of the brain receives inputs from many different neurons and can be affected by multiple sensory, motor, cognitive, and limbic modalities. Therefore, there is more than one means to affect a given neuron, and thus activating as many of those ways as possible and in a synchronized pattern would elicit artificial and strong activation of that neuron to alter its state. Repetitive activation of that neuron or groups of neurons would then lead to long-term plasticity, shifting it away from the abnormal state and suppressing the neurological condition (e.g., tinnitus). The treatment may need to be applied periodically since it may not cure the neurological condition but rather eliminate the debilitating symptoms.

One embodiment of this approach is for tinnitus suppression that applies coordinated activation of auditory and somatosensory pathways. A topographic organization of neurons within the auditory midbrain was discovered that can be differentially activated by different body locations in guinea pig. In other words, stimulation of different combinations of body locations with appropriate delays appears to activate different and specific neurons across the auditory midbrain, which in turn projects to other regions throughout the auditory system through ascending and descending pathways. Thus, a treatment described herein enables localized auditory activation without having to actually implant an electrode into the brain. Customized acoustic stimuli can then be used to reinforce or interact with those activated midbrain neurons that in turn would modulate and potentially induce plasticity across the auditory system. Other embodiments of this treatment would incorporate other reinforcement inputs, such as visual cues, cognitive/emotional effects, reward/pleasurable stimuli, and slightly painful stimuli that could all contribute to synchronization and enhanced plasticity within the brain.

This multi-modal synchronization therapy is not limited to treating tinnitus. For example, it could be used to treat phantom limb pain. Specific parts of the phantom limb or other somatosensory pathways could be stimulated (e.g., using current, pressure, or temperature stimuli) to activate neurons linked to or interacting with the pain that are then altered and reinforced by activation of the other modalities. For cognitive or emotional disorders, the activation process may be more complex but this approach could still be effective. For example, if the patient has a memory or learning issue, cognitive tasks that are already used in the field can be implemented. What is innovative about the approach described herein is the combination of these standard tasks with activation of other modalities. It is possible to provide coordinated body stimulation or even slightly painful but comfortable electrical shocks on the body in combination with a task. Not only could this induce synchronized activation of target brain regions, but it would also lead to elevated states of anxiety or excitement, naturally releasing neurotransmitters that could enhance plasticity and reinforcement to the task. This approach may be combined with stimuli to induce anxiety and increased attention, which in turn could enhance the plasticity to drive the neural changes back to normal. Other types of neurological disorders or deficits that are associated with abnormal and reversible neural patterns could also benefit from this multi-modal synchronization and noninvasive approach. This includes pain, body tremors, motor deficits, hyperacusis, and even psychological and mental disorders (e.g., obsessive compulsive disorder, depression, stress, memory or learning disability, speech impediment, and visual/auditory hallucinations).

There are numerous studies showing that activation of the limbic system as well as stimulation of the nucleus basalis, locus coeruleus, vagus nerve, and pedunculopontine nucleus can enhance plasticity within the brain, including the auditory system. However, direct stimulation of these regions within the brain requires invasive surgery. An alternative to this approach is to noninvasively and naturally activate the brain to release similar types of neuromodulators (e.g., acetylcholine, epinephrine, norepinephrine, serotonin, and dopamine) that can enhance plasticity. Certain embodiments of the treatments described herein are based on providing an unexpected and slightly painful stimulus that is synchronized with activation of other modalities. This unexpectedness will create anxiety and increased attention to the different stimuli, which in turn would naturally release neuromodulators required for brain plasticity. This release of neuromodulators can occur by activation of pathways through the pedunculopontine nucleus and amygdala that also interact with the nucleus basalis, locus coeruleus, and other limbic regions associated with attention, awareness, and emotion.

Experiments have been performed by electrically stimulating the pedunculopontine nucleus combined with acoustic stimuli and have shown the ability to alter firing patterns within the inferior colliculus. Not only is it possible to suppress or enhance acoustic-driven and spontaneous firing activity, it is also possible to shift the frequency tuning sensitivity of the neurons. These changes can last for tens of minutes to hours. These types of changes should enable modulation of abnormal patterns associated with tinnitus. As described herein, the auditory cortex has been stimulated in combination with acoustic stimulation and altered coding properties within the inferior colliculus, which in turn projects throughout the auditory system via ascending and descending pathways. Therefore, activation of limbic and descending pathways can contribute to neural plasticity throughout the auditory system.

For future experiments, the effects of unpredictability-based stress and anxiety response therapy (USAR therapy) in awake and behaving animals, including those with tinnitus, will be conducted. For USAR therapy, a slightly painful shock to the animals will be delivered while recording in the pedunculopontine nucleus, nucleus basalis, locus coeruleus, and other limbic centers to demonstrate that heightened anxiety and attention can alter firing patterns in these regions. However, it will be important to then combine this unexpected shock stimulus with acoustic stimuli, somatosensory stimuli, and activation of other modalities to demonstrate that firing patterns can actually be modified within the inferior colliculus and throughout the auditory system. To demonstrate that these different limbic pathways are involved, it is possible to lesion or inactivate (e.g., using optogenetic methods or local drugs) those regions and show that less or no plasticity changes occur in the auditory system. These experiments can be conducted in tinnitus animals to confirm that abnormal tinnitus patterns can be suppressed or reversed to eliminate behavioral tinnitus. Since the treatment approaches are noninvasive and use safe methods, the findings can be confirmed from these animal studies directly in humans by monitoring the tinnitus percept while implementing different combinations of parameters.

Direct brain stimulation (DBS) to treat various neurological disorders has become more widely accepted over the past decade due to its success, especially for tremor suppression in Parkinson's and Essential Tremor patients. However, it still requires invasive surgery and can only be justified in a small patient population. For tinnitus, there have been attempts at stimulating the cortex, midbrain, brainstem, and other non-auditory deep brain structures, but only in patients with debilitating conditions or who are already undergoing other types of neurosurgical operations (e.g., epilepsy surgery, tumor removal). To treat a larger population, non-invasive methods have been investigated. Previous methods attempt to modulate and drive precise plastic restoration of the auditory system using non-invasive stimulation that are not generally capable of precise or specific activation. An promising aspect of the methods described herein are that they activate a neural switch mechanism to reset the tinnitus-affected neurons back to normal using precisely synchronized stimulation across multiple sites rather than attempt to drive precise plasticity with continuous pulse stimulation (e.g., constant 100 Hz pulse train) on a given site. At least two brain regions, ICX and PPT, have been identified which can be stimulated to alter neural activity within the ICC and the central auditory system. An important aspect, in certain embodiments, is to non-invasively activate the ICX and/or PPT neural switch regions. Sufficient synchronized activity needs to be generated during stimulation of ICX or PPT combined with sufficient acoustic activation to be successful. Fortunately, ICX and PPT (also CNX, MGX, other reticular activating and limbic nuclei) receive converging and excitatory projections from all over the head, face, ears, eyes, mouth, tongue, neck, body, limbs, and genital areas as well as from the auditory and somatosensory cortices (FIG. 1). As described herein, it is possible to electrically activate these pathways non-invasively and simultaneously through transcutaneous stimulation to elicit a neural shock within the brain that activates the neural switch. It is possible to position surface electrodes (e.g., 20, 100 or 1000) over the body and limbs (e.g., feet, legs, shoulders, back, arms, fingers, genital areas) as well as the neck, pinna, cheeks, eye region, nose, tongue, teeth, and forehead. For safety, the goal is to use low level current on each site but across many sites to elicit a highly synchronous response in the neural switch regions. It is also possible to use non-invasive cortical stimulation (e.g., surface or transcranial magnetic stimulation) to activate the descending cortical projections and shine light into the eye to activate optic nerve projections to contribute to the neural shock. Smell and taste inputs are also able to project to overlapping brain regions that would then activate these neural switch regions, and thus it is possible to provide scent and taste stimuli as well.

Transcutaneous stimulation in humans will be initially implemented. Other non-invasive techniques will also be assessed to activate the skin surface and the corresponding nerve projections through vibration, pressure, heat, optics, or ultrasound. If more specificity and synchronization is required in certain circumstances, minimally-invasive wireless electrodes may be implanted, e.g., subcutaneously or around specific nerves. As an alternative, there are numerous invasive devices already in use and implanted in regions all over the brain that can be considered for eliciting sufficient shock stimulation through synchronized activation across all these different modalities.

The described treatment can provide a powerful way to noninvasively modulate tinnitus-affected neurons. It can also be implemented with low cost hardware and surface electrodes that can be easily miniaturized for portability and take-home usage, expanding on transcutaneous electrical nerve stimulation (TENS) devices safely used for pain or massage therapy (e.g., 2-site devices <$50 can already be purchased in stores). In order to investigate the numerous stimulation parameters directly in humans and identify the optimal settings, it is possible to pursue what is termed a heuristic translational approach. A low cost device can be implemented that could be distributed across a large patient group and taken home for continuous optimization by the patients. The simplest example would be to have a digital device with a knob that can scroll through the different stimuli that are preset during the clinical fitting session. The patient would input a rating into their device for each setting that effectively reduces their tinnitus. The device would continue to adjust the stimulation parameters based on these ratings to converge towards an optimal setting. Self-fitting through a heuristic translational approach is how the treatment can be fitted across a large number of patients and stimulation parameters. The patients are able to invest a considerable amount of time optimizing their own device. Any signs of improvement in their tinnitus with this treatment will provide significant motivation for the patients to continue optimizing their own device. Another advantage of a heuristic translational approach is that it is not necessary to understand the neural mechanisms of each type of tinnitus to improve the treatment. Instead, the device is heuristically optimized for each patient, which can overcome the issue of patient variability. The patients could also connect to an online server and database in which they can download new software for their device as well as upload their device parameters and progress. This online interaction with the patients would allow collection an enormous amount of data across a large population to identify appropriate stimulation patterns for different types of tinnitus patients. The patients can also interact with other patients and skilled personnel to help each other as well as improve the tinnitus treatment.

An innovation of multimodal stimulation therapy (MST) is that it can potentially achieve both specificity and non-invasiveness, and be optimized using a heuristic translational approach. MST takes advantage of the dense and coordinated interconnectivity across sensory, motor, cognitive, and limbic centers. One center may exhibit abnormal activity driving the neurological disorder. A goal of MST is to activate specific pathways related to the other modalities to then modulate and fix the abnormal region. This assumes that these different pathways can interact and induce plasticity across centers, which seems likely considering the necessity of precise coordination and reinforcement among these modalities during daily function and survival. MST can be used for tinnitus suppression through coordinated activation of auditory and somatosensory pathways. It is also possible to incorporate additional reinforcement, such as visual cues, cognitive and emotional activation (e.g., through mental tasks or emotional visual scenes), reward/pleasurable input (e.g., aromatherapy or soothing body sensations), or slightly painful stimuli. Another potential MST application is the treatment of phantom limb pain. Analogous to presenting customized acoustic stimuli to activate specific auditory neurons linked to tinnitus, specific parts of the phantom limb could be stimulated (e.g., using current, pressure, or temperature stimuli) and reinforced by activation of the other modalities. For cognitive or emotional disorders, the activation process may be more complex but the MST approach could still be effective. For example, if the patient has a memory or learning issue, cognitive tasks that are already used in the field can be implemented. What is innovative about MST is that these standard tasks can be combined with activation of other modalities. It is possible to provide coordinated body stimulation or even slightly painful but comfortable electrical shocks on the body in combination with a task. Not only could this induce synchronized activation of target brain regions, but it would also lead to elevated states of anxiety or excitement, naturally releasing neurotransmitters that could enhance plasticity and reinforcement to the task.

Integrative Role of Inferior Colliculus Relevant for the Treatment

The inferior colliculus (IC) is the principal midbrain nucleus of the auditory pathway and receives input from several more peripheral brainstem nuclei in the auditory pathway, as well as inputs from the auditory cortex. The inferior colliculus has three subdivisions: the central nucleus (ICC), a dorsal cortex by which it is surrounded, and an external cortex, which is located laterally. Its multimodal neurons are implied in auditory-somatosensory interaction, receiving projections from somatosensory nuclei. The input connections to the inferior colliculus are composed of many brainstem nuclei. All nuclei except the contralateral ventral nucleus of the lateral lemniscus send projections to the central nucleus bilaterally. It has been shown that a great majority of auditory fibers ascending in the lateral lemniscus terminate in the central nucleus. In addition, the IC receives inputs from the auditory cortex, the medial division of the medial geniculate body, the posterior limitans, suprapeduncular nucleus and subparafascicular intralaminar nuclei of the thalamus, the substantia nigra, pars compacta lateralis, the dorsolateral periaqueductal gray, the nucleus of the brachium of the inferior colliculus, deep layers of the superior colliculus, reticular activating nuclei, limbic nuclei, and other modulatory centers. The inferior colliculus receives input from both the ipsilateral and contralateral cochlear nucleus and respectively the corresponding ears. The medial geniculate body is the output connection from inferior colliculus and the last subcortical way station. The medial geniculate body is composed of ventral, dorsal, and medial divisions, which are relatively similar in humans and other mammals. The ventral division receives auditory signals from the central nucleus of the IC.

Certain embodiments of the invention will now be illustrated by the following non-limiting Examples.

EXAMPLE 1

The experiments described herein focus on plasticity experiments to confirm that a dual fixed-plastic representation exists for features relating to tinnitus, such as tonotopy, firing rates, synchrony, and bursting. Other experiments involve direct stimulation of ICX, CNX, MGX, reticular activating nuclei, and limbic centers to assess the neural switch effect within the ICC, CNV, MGV, and A1 in normal hearing and tinnitus animals. Other experiments identify the non-auditory projections that can be simultaneously activated with subcutaneous electrical stimulation or surface manipulation (e.g., pressure, gentle stroking, air puffs, pinching) to elicit a synchronous response in the different neural switch regions and to suppress tinnitus-driving neurons within the central auditory system.

The plasticity experiments will use earplugs that will predominantly attenuate high frequencies. These can be used in guinea pigs, and later in humans, to create a temporary high frequency hearing loss. Unlike traditional methods of permanently damaging the peripheral auditory system through noise, drugs, or mechanical manipulations, the earplugs can be inserted and removed to reversibly alter the hearing condition. High frequency hearing loss situations can be induced that allow the brain to reorganize in terms of tonotopy and firing patterns across neurons. The earplugs can then be removed, and acoustic stimulation presented to accurately characterize the neurons within the CNV, ICC, MGV, and A1, which is not possible with traditional deafening methods. More importantly, to demonstrate the dual fixed-plastic representation within the brain, it is possible to re-expose the animal to natural sounds by removing the ear plugs and show that the original tonotopy and firing patterns return quite quickly. The earplugs can also be re-inserted and removed repeatedly to assess how quickly and accurately the brain switches back and forth between brain states. The animals will be implanted chronically with electrode arrays or a special chamber to allow arrays to be re-inserted at different time points. Several head screws will also be implanted on the skull to allow non-invasive connection for EEG recordings to more frequently monitor the plastic changes over time. Using this creative earplug paradigm, all the different neural switch regions can be electrically stimulated and assessed to switch the brain back and forth between the original and reorganized states.

It is possible to induce tinnitus in guinea pigs using two common methods relevant for the types of tinnitus observed in humans: (1) loud noise exposure, and (2) ototoxic drugs (e.g., salicylate). Chronic electrode arrays (e.g., 32-64 site arrays) can then be implanted into different auditory and neural switch regions. A special chamber will be implanted on the skull for re-inserting arrays with degraded recordings. Tinnitus in animals will be assessed before and after the synchronized stimulation paradigm, and also determine the duration and stability of suppression over repeated stimulus presentations. The neural activity and electrode site locations based on histological brain reconstructions will be correlated with the perceptual effects.

Ultimately, this therapy will be used in humans to suppress a phantom percept across a wide range of patients, such as tinnitus patients. A phantom percept refers to the conscious awareness of a percept in the absence of an external stimulus. Examples of phantom percepts are tinnitus and phantom limb (e.g., phantom limb pain). The treatment will be tested across a large range of tinnitus animals and the perceptual effect will be behaviorally confirmed. The startle response will be used to assess tinnitus perception in animals. This is a creative method developed by Turner and colleagues at Southern Illinois University that does not require time consuming animal training but is based on a simple reflex response. A loud unexpected sound burst will cause an animal to startle and can be measured with a force plate. If a soft short sound (or short gap in a continuously played soft sound) precedes this loud sound (i.e., the pre-burst stimulus), it reduces the animal's startle response. If an animal has tinnitus, the pre-burst stimulus can be aligned with and masked by the tinnitus percept. In this case, animals with tinnitus will not have a reduced startle response to the pre-burst stimulus. The startle response method has been used successfully by numerous researchers worldwide.

By synchronizing the electrical shock with acoustic stimulation, long lasting enhancement or suppression of firing activity can be induced that is highly dependent on the delay between the stimuli. Improper timing could worsen (enhance) rather than suppress the tinnitus. Non-invasive evoked EEG activity will be used to monitor the stimulation effects since it is designed to record synchronous activity and can be correlated with direct recordings of the different auditory and neural switch regions. In patients, an automated algorithm can be used that would stimulate across different combinations of sites with varying delays until the largest EEG response was elicited with an appropriate pattern across recording sites, indicating a highly synchronous shock within the appropriate brain region. The number of EEG electrode sites and locations as well as activation pattern will initially be based on findings from animals. The time delay for the electrical shock alone and the acoustic stimulus alone to each reach the neural switch region based on the evoked EEG response latency will be measured. Based on these timings, the algorithm would determine the appropriate delay between the synchronized acoustic and electrical stimuli to suppress rather than enhance the tinnitus. This algorithm will be used to ensure it identifies the appropriate parameters within a reasonable time period. Fortunately, each EEG response can be collected quite quickly (<100 ms).

A subjective approach that will run in parallel with the objective EEG approach is also to create a user interface that allows the subject to scroll through the different parameters. There will be a large parameter space. However, it is possible to scroll through a subset of parameters and then select the few that can affectively alter and improve the tinnitus percept. Then the interface determines the next best parameters based on the past successful parameters. Through continued use and iterations of this algorithm, the interface will be able to identify the optimal parameters over time. This would involve development of low cost technologies and stimulators that can be easily positioned all over the body and head and intuitive to use across a large patient population. The device would also be connected to the internet to allow real-time data collection, analyses, and feedback to make parameter identification more efficient. The data would be collected across a large patient population and can then be rapidly collected and assessed for which parameters work most effectively for the different tinnitus types. In turn, these data would guide the initial parameter space for each proceeding subject. Therefore, a new heuristic approach to performing translational research directly in humans is proposed using non-invasive strategies, internet technologies (e.g., online programs, databases, and smart apps), and parameter optimization/assessment performed by the patients themselves.

EXAMPLE 2. UNPREDICTABILITY BASED METHOD FOR TREATING TINNITUS AND OTHER NEUROLOGICAL DISORDERS

This approach is based on similar concepts as the multimodal stimulation therapy (MST) approach in that it shifts brain regions linked to tinnitus to suppress the phantom percept (and relevant to other neurological disorders with similar types of "bad" plasticity). In the MST, synchronized stimulation across multiple body and head regions is used to elicit synchronized shocks in both auditory and non-auditory brain regions to shift plasticity back to normal. One of the features for the MST therapy is the ability to activate specific brain regions (e.g., limbic and arousal centers) that can then reinforce the simultaneous acoustic driven activity that could suppress the tinnitus percept. Another feature of MST is the ability to achieve these effects with non-invasive stimulation. In the approach described in this example, which is termed "Unpredictability-based Stress and Anxiety Response therapy (USAR Therapy), acoustic stimulation is still presented as well as the option to perform MST. However, an additional innovative aspect of the USAR therapy is that the limbic and arousal centers are activated, e.g., using a behavioral approach. The creative idea is to provide a painful yet acceptable electrical stimulus to different parts of the body (or any other type of painful or startle stimulus, such as a loud sound burst or scary visual image or pinch). A key feature is that the tinnitus patient does not know when or where this stimulus will be presented. This unpredictability and uncertainty will put the patient into a stressful and anxious state. This in turn will activate multiple limbic, arousal, and attentive centers and release a wide range of hormones and neurotransmitters involved with plasticity and reinforcement. This release itself is not sufficient to treat the tinnitus, though it could alter the tinnitus percept as has been shown with various drugs. An important component is to present acoustic stimuli synchronized to this painful stimulus to reinforce those acoustic inputs. One scenario would be to play all frequencies except the main frequency component of the tinnitus which would in turn reinforce all the other stimuli to begin to dominate the tinnitus stimulus component. This would begin to suppress the dominance of the tinnitus percept. Another scenario is to present randomized acoustic stimuli spanning across a wide range of features, even the tinnitus features that would desynchronize and dilute the specific effects of the tinnitus percept. It is possible to use drugs to release hormones and neurotransmitters and then present acoustic stimuli as well as the MST to treat tinnitus. However, in this drug-based scenario, there is no precisely timed reinforcement of the drug effects with the acoustic and electrical stimulation. By inducing anxiety and stress with this unpredictable and painful stimulus, the patient's brain will not only be exposed to these different hormones and neurotransmitters, but will also release these chemical that can be synchronized to the painful stimulus that provides a precise manner to shift the brain back to normal, optionally in combination with MST. Furthermore, this approach does not rely on introducing any potentially harmful substance into the body but uses the body's own hormones and neuro-chemicals to achieve the effect while also being non-invasive. The device would consist of similar components as the MST except that one site (or several sites) would be stimulated with a painful stimulus. The patient can be focusing on a screen to indicate that a painful stimulus will be presented within a specific time period (e.g., 30 s) that at least provides some organizational information to the patient (i.e., the patient knows what to be doing at a certain time) and is also a way to systematically alter the patients attention and interactions with the treatment (e.g., a patient performs a task during this paradigm to distract or increase focus on the painful stimulus that could vary the overall reinforcement effect). Since the anxiety and stress, and thus the neuro-chemical, induced by the USAR therapy will adapt over time (i.e., become weaker with repeated stimulation), it will be important to provide on and off periods of treatment. It will also be important to alter the sites and pattern of unpredictability to continue to release the necessary neuro-chemicals for longer periods of time. These effects can be varied by altering the stimulation strategies as well as the type of pain or startle stimulus used.

This approach may be applied to other neurological disorders that involve abnormal plastic states. This can be a significant opportunity to treat an even larger patient population, such as those experiencing pain or even cognitive/emotional changes. For example, for someone experiencing phantom pain, there would be changes in the somatosensory system. This system also receives multi-modal inputs and processing. In this case, an unpredictable and loud startle sound stimulus and/or disturbing visual image can be presented and combined that with somatosensory body stimulation. This could also be combined with MST. Another example would be someone experiencing a learning or cognitive deficit. That person could perform a mental task combine with USAR Therapy and MST to reinforce the neurons related to that task and enhance learning or cognitive capacity.

These findings are surprising in many respects because it is actually counterintuitive to attempt to induce stress and anxiety to suppress tinnitus because tinnitus induction is usually associated with greater stress and anxiety. However, the logic is based on synchronizing appropriate activation of specific auditory and non-auditory regions to this painful/startle stimulus to increase the dominance of other sound components that would dilute the contribution of the tinnitus sound component (i.e., so make the brain more sensitive and attentive to other sound components and thus making it relatively less sensitive to the tinnitus component). Alternatively, this approach could activate multiple neurons, including those representing the tinnitus percept, to then drive desynchronization and plasticity across those neurons to eliminate the phantom percept.

EXAMPLE 3. MAPPING THE INFERIOR COLLICULUS

Applicants have conducted experiments demonstrating that neurons along the dorsal region of the IC code for different body regions in a spatially-ordered pattern. It was found that upper body regions generally activate more lateral regions of the IC while lower body regions generally activate more medial IC regions. It was found that left body regions activate more rostral-medial regions compared to those for the right body regions. Overall, it was found that the toe-to-head body orientation is superimposed onto the caudal-medial to rostral-lateral axis of the IC. There are also overlapping regions of IC that are activated by different body sites and with varying delays. Therefore, based in part on this work, specific regions of the IC can be activated by stimulating the appropriate body sites with the appropriate delays.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A method for treating a patient having a neurological disorder or deficit, comprising delivering to the patient at least one synchronized stimulation, wherein the synchronized stimulation comprises an effective delivery of synchronized stimulation to the patient's brain from at least one auditory neuronal pathway synchronized with stimulation from at least one somatosensory neuronal pathway, wherein the delivery of stimulation to the auditory neuronal pathway and the stimulation to the somatosensory neuronal pathway are synchronized for delivery via a device, wherein the neurological disorder or deficit treated is tinnitus and/or hearing loss.

2. The method of claim 1, wherein the neurological disorder or deficit is tinnitus.

3. The method of claim 1, wherein the neurological disorder or deficit is hearing loss.

4. The method of claim 1, wherein the synchronized stimulation involves a stimulus pattern lasting between 0.01 to 100 ms for each activated pathway with a specifically determined time between each activated pathway that ranges between 0-1000 ms.

5. The method of claim 1, wherein in the at least one somatosensory neuronal pathway is a sensory pathway from the patient's head, face, ear, eye, nose, mouth, lip, tongue, tooth, neck, body, limb, genital areas, buttocks/anus regions, hand, finger, foot, or toe.

6. The method of claim 1, wherein multiple discrete synchronized stimulations are delivered every 100 to 10000 ms apart for a total duration ranging from 1 s to 1 hour that can be repeated as many times as needed for treatment.

7. The method of claim 1, wherein the stimulation from the at least one somatosensory neuronal pathway is evoked by non-invasive stimulation.

8. The method of claim 7, wherein the stimulation from the at least one somatosensory neuronal pathway is evoked by transcutaneous electrical stimulation, mechanical vibration or pressure applied to the skin surface.

9. The method of claim 8, wherein the stimulation from the at least one somatosensory neuronal pathway is evoked by transcutaneous electrical stimulation.

10. The method of claim 8, wherein the stimulation from the at least one somatosensory neuronal pathway is evoked by mechanical vibration or pressure applied to the skin surface.

11. The method of claim 8, wherein the delivery of stimulation to the auditory neuronal pathway is via headphones.

12. The method of claim 1, wherein the synchronized stimulation modulates tinnitus-affected neurons to treat the tinnitus/hearing loss.

13. The method of claim 1, the method comprising: identifying synchronized multi-modal stimulation parameters comprising timing, intervals, and/or ordering of an auditory stimulation signal and a somatosensory stimulation signal, the auditory stimulation signal and the somatosensory stimulation signal forming a synchronized multi-modal stimulation to be applied to treat the patient, wherein the multi-modal stimulation parameters are identified to produce a reduction in an objective measure of neural correlates of the tinnitus in the patient based at least in part on at least one of: tested differences in timing between the auditory stimulation signals and the somatosensory stimulation signals, tested differences in intervals between the auditory stimulation signals and the somatosensory stimulation signals, and tested ordering of the auditory stimulation signals and the somatosensory stimulation signals; and treating the patient by applying both the synchronized auditory stimulation signal to the auditory system of the patient with the somatosensory stimulation signal to the somatosensory system of the patient, in accordance with the synchronized timing, intervals, and/or ordering of the multi-modal stimulation parameters thereby treating the tinnitus of the patient.

14. The method of claim 13, wherein applying the auditory stimulation signals and the somatosensory stimulation signals to the patient according to the varying parameters comprises: adjusting one or more of a timing, an interval between, and an ordering between the auditory stimulation signals and the somatosensory stimulation signals.

15. The method of claim 13, wherein identifying the multi-modal stimulation parameters comprises: applying auditory stimulation signals and somatosensory stimulation signals to the patient according to varying parameters; assessing effects of the auditory stimulation signals and the somatosensory stimulation signals on the patient as parameters are varying, wherein the assessing is performed by measuring a response of the patient using an electroencephalography test; and in response to the assessing, identifying the multi-modal stimulation parameters as the timing, intervals, and/or ordering that reduce the tinnitus in the patient treated.

16. The method of claim 13, wherein identifying the multi-modal stimulation parameters comprises: applying auditory stimulation signals and somatosensory stimulation signals to the patient according to varying parameters; assessing effects of the auditory stimulation signals and the somatosensory stimulation signals on the patient as parameters are varying, wherein the assessing is performed by measuring a responsiveness of the patient using an electroencephalography test; and in response to the assessing, identifying the multi-modal stimulation parameters as the timing, intervals, and/or ordering that reduce the tinnitus in the patient treated.

17. The method of claim 13, wherein identifying the multi-modal stimulation parameters comprises: applying auditory stimulation signals and somatosensory stimulation signals to the patient according to varying parameters; assessing effects of the auditory stimulation signals and the somatosensory stimulation signals on the patient as parameters are varying, wherein the assessing is performed by measuring a patientive response of the patient using the patient's perception of tinnitus; and in response to the assessing, identifying the multi-modal stimulation parameters as the timing, intervals, and/or ordering that reduce the tinnitus in the patient treated during the treatment mode.

18. The method of claim 13, the method further comprising identifying the multi-modal stimulation parameters for the timing, the intervals, the ordering, frequency, and/or amplitudes of the auditory stimulation signal and the somatosensory stimulation signal.

19. The method of claim 13, wherein the auditory stimulation is caused by sound, wherein the sound is delivered using headphones and is one or more pure tone frequencies, bandwidth filtered sinusoids or noise.

20. The method of claim 13, wherein the somatosensory stimulation signal is caused by transcutaneous electrical nerve stimulation (TENS) delivered using a TENS unit, wherein the delivery of the sound from the headphones and the somatosensory stimulation from the TENS unit is synchronized and delivered by a device having a user interface to adjust the stimulation pattern to treat the tinnitus.

* * * * *

UNITED STATES PATENT AND TRADEMARK OFFICE
CERTIFICATE OF CORRECTION

PATENT NO. : 10,940,315 B2
APPLICATION NO. : 16/362001
DATED : March 9, 2021
INVENTOR(S) : Hubert H. Lim et al.

Page 1 of 1

It is certified that error appears in the above-identified patent and that said Letters Patent is hereby corrected as shown below:

In the Specification

Column 8, Line 11, "gyms" should be --gyrus--.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*